United States Patent
Nakano et al.

(10) Patent No.: US 7,875,387 B2
(45) Date of Patent: Jan. 25, 2011

(54) ELECTRODE FOR USE IN ELECTROCHEMICAL DEVICE, SOLID ELECTROLYTE/ELECTRODE ASSEMBLY, AND PRODUCTION METHOD THEREOF

(75) Inventors: Hiroshi Nakano, Chikusei (JP); Hiroshi Yoshida, Mito (JP); Masatoshi Sugimasa, Tokai (JP); Katsumi Mabuchi, Hitachi (JP); Haruo Akahoshi, Hitachi (JP)

(73) Assignee: Hitachi Cable, Ltd., Tokyo (JP)

( * ) Notice: Subject to any disclaimer, the term of this patent is extended or adjusted under 35 U.S.C. 154(b) by 1080 days.

(21) Appl. No.: 11/518,204

(22) Filed: Sep. 11, 2006

(65) Prior Publication Data

US 2007/0059584 A1    Mar. 15, 2007

(30) Foreign Application Priority Data

Sep. 13, 2005    (JP) .............................. 2005-265017

(51) Int. Cl.
*H01M 4/78* (2006.01)
*H01M 4/02* (2006.01)

(52) U.S. Cl. ..................................................... 429/209
(58) Field of Classification Search .................. 429/209
See application file for complete search history.

(56) References Cited

U.S. PATENT DOCUMENTS 1,846,329 A * 2/1932 Newton Harrison ......... 429/161

2005/0064291 A1 * 3/2005 Sato et al. .................... 429/233
2005/0074671 A1 * 4/2005 Sugiyama et al. ...... 429/231.95

FOREIGN PATENT DOCUMENTS

JP          50-36935       4/1975
JP          2004-349164    12/2004

* cited by examiner

*Primary Examiner*—Gregg Cantelmo
(74) *Attorney, Agent, or Firm*—Antonelli, Terry, Stout & Kraus, LLP.

(57) ABSTRACT

In an electrode in electrochemical device, particularly an anode lithium ion secondary battery, a cathode for use in alkali storage battery, an electrode for use in fuel cell, or a capacitor electrode, a metal structure has nano size micro-pillars is constructed with an electrode active material being formed on the surface of the metal structure. The metal structure having nano size micro-pillars can be formed, for example, by forming a metal layer as an electrode material by plating to the surface of a substrate having pores and then removing the substrate by dissolution, the metal filled in the pores of the substrate to form a group of micro-pillars. And the active material can be formed by depositing metal by plating. Since the active material is in direct contact with the conductive skeleton, the conducting agent for connecting the active materials to each other may not be added at all.

15 Claims, 5 Drawing Sheets

ELECTRODE FOR USE IN ELECTROCHEMICAL DEVICE, SOLID ELECTROLYTE/ELECTRODE ASSEMBLY, AND PRODUCTION METHOD THEREOF

CLAIM OF PRIORITY

The present application claims priority from Japanese application serial No. 2005-265017 filed on Sep. 13, 2005, the content of which is hereby incorporated by reference into this application.

Field of the Invention

The present invention relates to an electrode for use in electrochemical device of converting, producing or depositing a material by electrochemical reaction. Further it relates to an assembly of an electrode and a solid electrolyte. Further it also relates to a production method thereof.

The present invention is suitable to be used as an electrode for use in electrochemical devices such as fuel cells, lithium ion secondary batteries, capacitors, and sensors.

BACKGROUND OF THE INVENTION

In recent years, along with popularization of mobile terminals such as mobile telephones or portable note type personal computers, importance of a power supply thereof receives widespread attention. It has been demanded for the power supplies that they are reduced in the size and the weight, as well as they have high capacity and are less deteriorated. Since a lithium ion secondary battery has a high operation voltage and high energy density, it is suitable as a battery for such mobile terminals. Further, a direct methanol fuel cell (DMFC) has also attracted attention as a power supply for mobile terminals.

In the lithium ion secondary battery, an electrode active material using $LiCoO_2$ or manganese spinel as a main ingredient has been used for a cathode material, and a carbon material including graphite has been used for an anode material. For molding the electrode active materials as an electrode, carbon particle or a binder referred to as a conductive aid material is used being kneaded with electrode active material. Then, the current flowing path includes a path in which current flows from the surface of the active material where electrode reaction proceeds, by way of skeletons such as the conductive aid material to the outside. However, since the electrode active material is particles independent from each other, the resistance is high and there are many particles not substantially contributing to the electrode reaction.

With an aim of enhancing the safety of the lithium ion secondary battery, it has been proposed to use a solid electrolyte. However, since it is difficult to uniformly contact the active material and the solid electrolyte to each other, this increases the active material not contributing to the electrode reaction.

Further, in the direct methanol fuel cell, a noble metal such as platinum referred to as a catalyst is supported as a nano size particle on a carbon material at each of the electrodes of the fuel electrode and the air electrode. Also for such electrodes, it has been proposed to use noble metal particles as the electrode being kneaded and molded with a binder and use the same in combination with a solid polyelectrolyte. However, it can not be said that they are utilized effectively, for example, in that the nano size catalyst is buried in the electrolyte.

Technical documents concerning the prior art include, for example, JP-A No. 2004-349164 and JP-A No. 50-36935.

The electrode of a battery comprises an active material contributing to the electrode reaction, a conductive aid material to be a conduction path for the active material and a current collector for flowing current externally. However, in a case where the active material is not physically bonded to the conductive aid material or in a case where the current flowing path from the active material to the current collector is long and, accordingly, the resistance is high, since the conduction path from the active material of the battery to the outside is restricted, it is considered that the internal resistance is high and an active material not capable of contributing to the electrode reaction is generated.

Further, an conventional electrode structure involves a problem of causing peeling between the active material and the conductive aid material due to volumic change or stress along with charge/discharge. Therefore, the deterioration of current collection or deterioration of capacity due to powderization may increase. Since the internal resistance of the battery increases due to the deterioration of the current collection, it also results in a problem capable of not obtaining a satisfactory battery characteristic. It is considered that they are caused by the following phenomenon. That is, expansion/contraction of a metal contained in the carbon material makes the density between particles constituting the electrode coarser. As a result, the conduction path decreases and, further, the conduction path becomes incomplete upon repeating charge-discharge, and then a portion not contributing to charge/discharge may occur.

It may be possible to improve the safety of the battery by using a polymer type solid polymeric membrane for the electrolyte. However, the conventional electrode structure has a problem that formation of interface is difficult between the active material of the electrode and the solid electrolyte membrane, as a result, active material not substantially capable of contributing to the reaction is present.

As described above, while the structure of the electrode in the electrochemical device has a great concern with the performance thereof but there exists a common subject that the active material can not yet been utilized effectively.

The present invention has been achieved in view of the foregoing problems and it intends to provide an electrochemical device-electrode having characteristics of high capacity and low resistance. Particularly, the present invention is applied to the electrode such as an anode for use in lithium ion secondary battery, a cathode for use in alkali storage battery, an electrode for use in fuel cell or a capacitor electrode.

SUMMARY OF THE INVENTION

In the invention, a metal structure having a group of nano size micro-pillars is proposed as the electrode, and a battery active material is formed on the surface of the metal structure. The metal structure having the nano size micro-pillars can be formed by the processing steps: namely, forming a metal layer as an electrode material by plating on the surface of a substrate having pores, and then removing the substrate by dissolution. The metal filled in pores of the substrate forms a group of micro-pillars. The active material can be formed by depositing a metal by plating.

According to the invention, an electrode where an active material is in direct contact with the surface of a metal structure as a current collector can be obtained without using a conductive aid material. Since the resistance of the electrode is small and the active material can be utilized effectively in the electrode of the invention, the capacity density of the electrode is improved by so much.

Preferred embodiments of the invention are described below.

(1) An electrode for use in an electrochemical device including a metal structure having a group of micro-pillars and an active material formed directly on the surface of micro-pillars of the metal structure.

(2) An electrode for use in an electrochemical device, in which the micro-pillars group like cilia on the surface of the metal structure.

(3) An electrode for use in an electrochemical device, in which the metal structure is formed of nickel or copper.

(4) An electrode for use in an electrochemical device, in which the active material is formed by depositing a metal to be active material by plating.

(5) A cathode for use in an alkaline storage battery, in which the metal structure having a group of micro-pillars comprises nickel, and nickel hydroxide is formed by electrochemical oxidation on the surface of the micro-pillars.

(6) An electrode for use in a capacitor, in which the metal structure having a group of micro-pillars comprises nickel, and nickel hydroxide is formed by electrochemical oxidation on the surface of the micro-pillars.

(7) An electrode for use in a fuel cell, in which the metal structure having a group of micro-pillars comprises nickel, ruthenium is formed by electrodeposition on the surface of the micro-pillars, and platinum is formed on the ruthenium.

(8) An electrode for use in a capacitor, in which the metal structure having a group of micro-pillars comprises nickel, ruthenium is formed by electrodeposition on the surface of the micro-pillars, and ruthenium oxide is formed by electrochemical oxidation thereon.

(9) An anode for use in a lithium ion battery, in which the metal structure having a group of micro-pillars comprises nickel, a nickel-tin alloy or tin-cobalt alloy is formed by electrodeposition on the surface of the micro-pillars and doped with lithium.

(10) An anode for use in a lithium ion battery, in which the metal structure having a group of micro-pillars comprises copper, a copper-tin alloy or tin-cobalt alloy is formed by electrodeposition on the surface of the micro-pillars and doped with lithium.

(11) An electrode for use in an oxygen concentration sensor, in which the metal structure having a group of micro-pillars comprises copper, and silver is formed by electrodeposition on the surface of the micro-pillars.

(12) A solid electrolyte/electrode assembly formed by joining an electrode and a solid electrolyte, in which the electrode comprises a metal structure having a group of micro-pillars and an active material formed directly on the surface of the micro-pillars of the metal structure.

(13) A solid electrolyte/electrode assembly described above, in which the active material is formed by depositing a metal to be the active material by plating.

(14) A solid electrolyte/electrode assembly, in which the micro-pillars of the metal structure are buried in the solid electrolyte.

(15) A solid electrolyte/electrode assembly, in which the metal structure is formed of nickel, the active material comprises ruthenium and platinum formed by electrodeposition, and the platinum is formed on the ruthenium.

(16) A solid electrolyte/electrode assembly described above, in which the metal structure is formed of copper, and the active material comprises a copper-tin alloy formed by electrodeposition.

(17) A method of producing an electrode for use in an electrochemical device, the method comprising steps of:

forming a metal layer to be an electrode material by plating on the surface of a substrate with pores, removing the substrate by dissolution, and thus forming a metal structure having a group of micro-pillars, and depositing a metal to be an active material by plating on the surface of the micro-pillars.

(18) A method of producing an electrode, for use in an electrochemical device, the method comprising steps of:

forming an alumina film with pores by anodic oxidation on the surface of an aluminum substrate;

forming a metal layer to be an electrode material by plating on the surface of the alumina film;

removing bottoms of the pores in the aluminum substrate by dissolution, and then forming micro-pillars by filling a metal to be an electrode material into the pores;

removing the alumina film by dissolution to obtain a metal structure having a group of micro-pillars; and depositing a metal to be an active material by plating on the surface of the micro-pillars of the metal structure.

(19) A method of producing an electrode for use in an electrochemical device described above, in which a seed layer is at first formed and then a metal layer is formed by plating on the seed layer in preparing a layer of a metal as an electrode material to the surface of the alumina film.

(20) A method of producing a solid electrolyte/electrode-assembly, A method of producing a solid electrolyte/electrode assembly, the method comprising steps of:

forming a metal layer to be an electrode material by plating on the surface of a substrate with pores, removing the substrate by dissolution, and thus forming a metal structure having a group of micro-pillars, depositing a metal to be an active material by plating on the surface of the micro-pillars, and thus making the electrode, and then pressing the electrode to the solid electrolyte to form an assembly in which the solid electrolyte and the electrode are integrated.

Since the electrode of the invention is used for an electrochemical device, it is preferred that the diameter of the micro-pillar is from 10 nm to 1 μm and the height is 100 nm to 50 μm. Further, the active material deposited on the surface of the micro-pillar is preferably platinum, ruthenium, nickel, palladium, cobalt, tungsten, molybdenum, copper, gold, silver, or tin. Further, the current collector portion of the electrode preferably comprises nickel or copper.

DETAILED DESCRIPTION OF THE PREFERRED EMBODIMENTS

EXAMPLE 1

Figure 1:
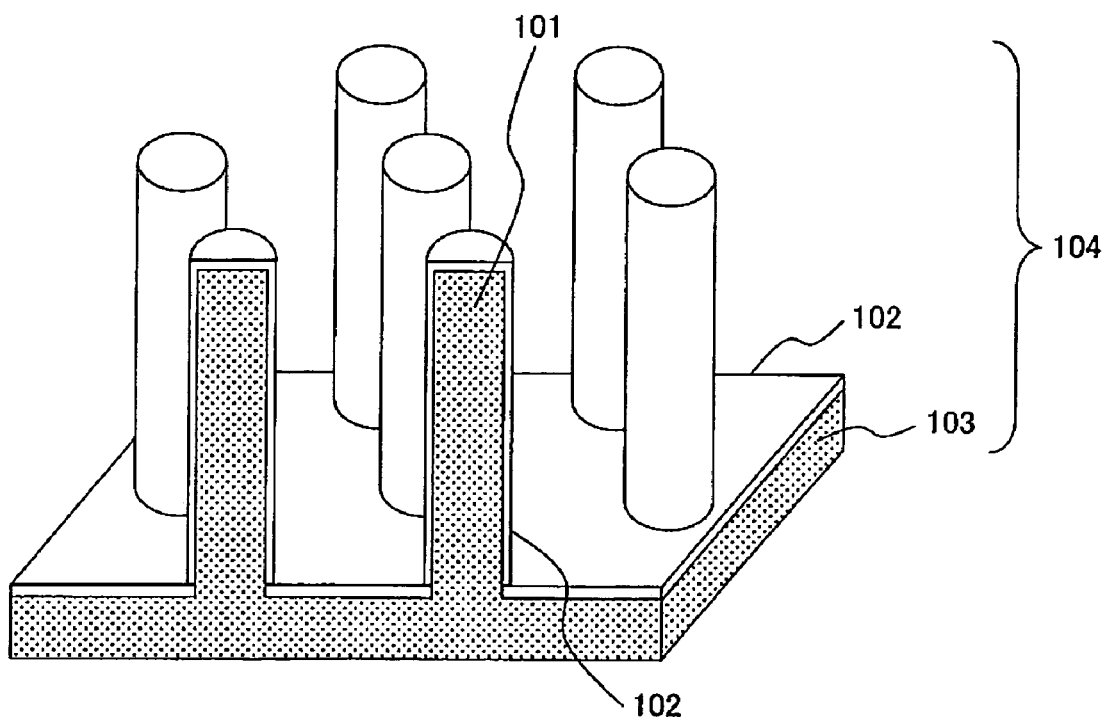
FIG. 1 is a perspective view showing an example of an electrode according to the invention.

FIG. 1 is a perspective view showing an example of an electrode for use in electrochemical device according to the invention. An electrode 104 comprises a metal structure 103 having a group of micro-pillars 101 formed on the surface thereon, and an electrode active material 102. While the shape of the micro-pillar is a cylindrical columnar in FIG. 1, it may be a square cylindrical columnar (pillar) 302, and cylindrical columnar pillars and square cylindrical columnar pillars may also be present together. There is no particular restriction for the micro-pillars.

The electrode for use in electrochemical device of the shape shown in FIG. 1 was produced by production steps shown in FIGS. 2A to 2F.

Figure 2:
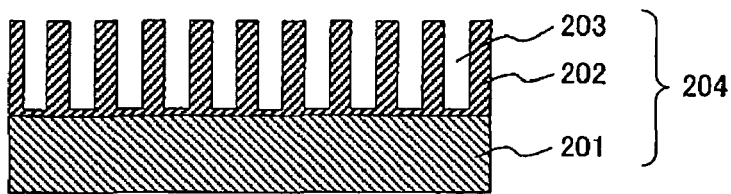
FIGS. 2A to 2F are flow charts showing production steps of the electrode shown in FIG. 1.
Figure 2:
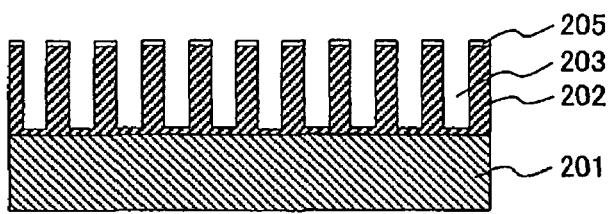
Figure 2:
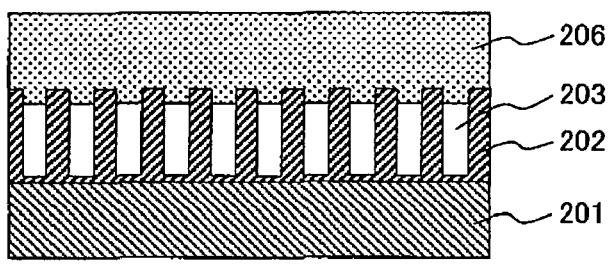
Figure 2:
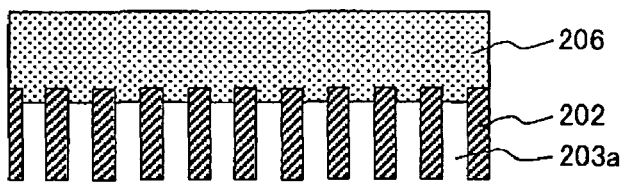
Figure 2:
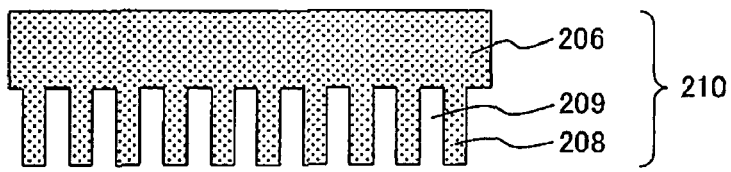
Figure 2:
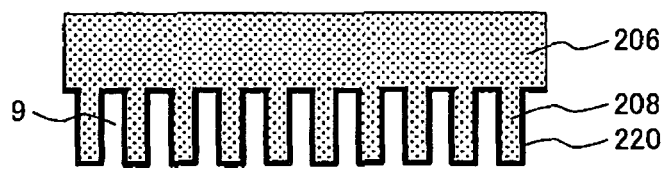
Figure 3:
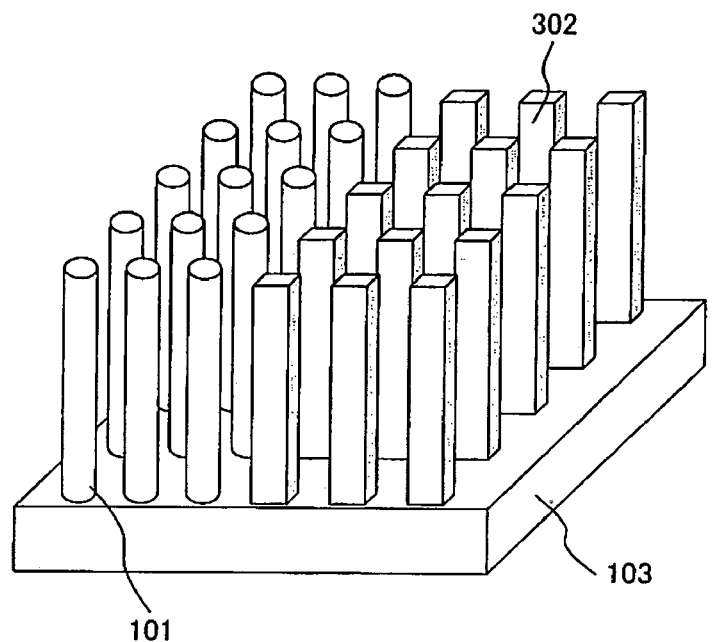
FIG. 3 is a perspective view showing another example of a metal structure having a group of micro-pillars.

FIG. 2A shows a substrate having pores. The substrate can be formed by anodic oxidation of an aluminum plate 201 in an acidic solution, for example, a solution of oxalic acid, chromic acid, or sulfonic acid. Anodized alumina 202 is formed on the surface of the aluminum plate 201, and pores 203 arranged regularly are obtained. The diameter of the pore 203 can be controlled to any size within a range from 5 to 200 nm by controlling the operating voltage. In a case of intending to increase the diameter of the pore 203 further, it is preferably dissolved by an acid solution after anodic oxidation, by which the pore can be dissolved to enlarge the pore diameter to about 1,000 nm. In a case of intending to increase the aspect ratio of the pore, the anodic oxidation is preferably conducted under a low temperature condition for a long time.

Then, a metal structure having pores is produced by using the substrate as a fine porous mold. In this example, a nickel seed layer 205 is formed at a thickness of about 50 nm by electroless plating onto the surface of anodized alumina 202 of the fine porous mold 204 having pores with the diameter of 30 nm in average and the depth of 10 μm. The nickel seed layer 205 may also be formed by a sputtering method or vacuum deposition method. The nickel electroless plating solution used herein is an NPR-4 solution manufactured by C.Uyemura & Co.,Ltd., and a deposited film is an alloy film of nickel and phosphorus containing about 7% phosphorus.

Then, as shown in FIG. 2B, a nickel film 206 was formed at a thickness of 15 μm by an electroplating method onto the nickel seed layer 205. While the nickel film 206 was formed by using a nickel sulfonate bath at a current density of 3 mA/cm$^2$ but this is not restrictive and a watts nickel bath, etc. can also be used. In this example, a solution formed by dissolving 360 g/dm$^3$ of nickel sulfonate, 5 g/dm$^3$ of nickel chloride, and 30 g/dm$^3$ of boric acid was used as the nickel sulfamate bath.

Then, the aluminum plate 201 was etched with mercury chloride and, successively, the pore bottoms of the pores 203 were dissolved by a phosphoric acid treatment at 0.3 mol/dm$^3$, and thus through holes 203a were made on the surface of the nickel film 206 as shown in FIG. 2D.

Figure 4:
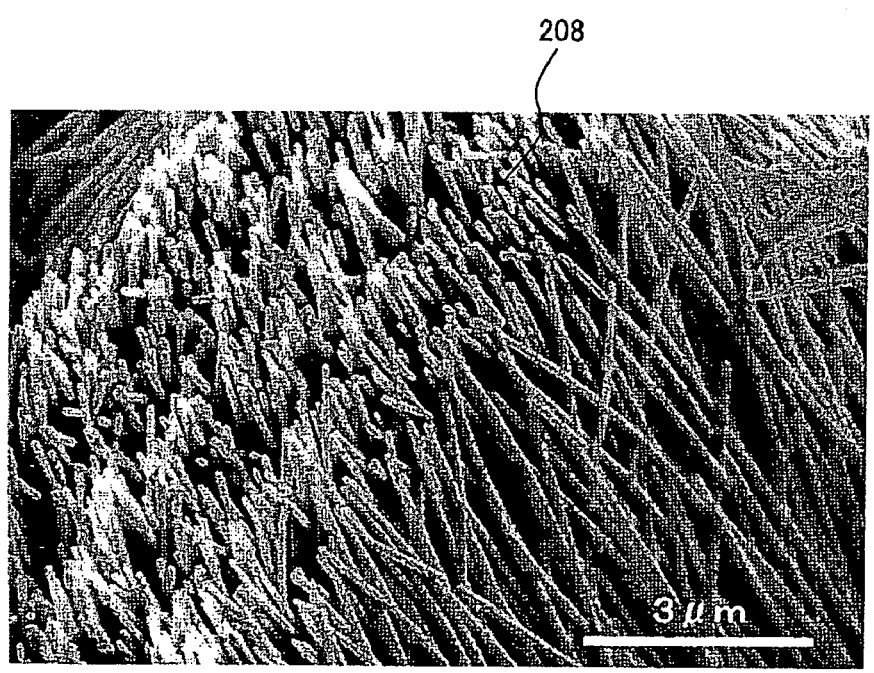
FIG. 4 is a microscopic photograph showing the shape of a group of micro-pillars.

Then, nickel was filled into the through holes 203a to form micro-pillars 208 by electroplating with nickel sulfamate. The micro-pillars 208 were formed at a current density of 0.5 mA/cm$^2$. Then, the remaining anodized alumina 202 was dissolved in 0.1 mol/dm$^3$ of a sodium hydroxide solution, to form pores 209. Thus, a metal structure 210 having pores was prepared as shown in FIG. 2E. The diameter of the micro-pillar 208 of the metal structure 210 obtained in this case was substantially equal with 30 nm for the pore diameter of the anodized alumina 202 used as the starting material, and the film thickness obtained was about 2 μm less than the hole depth of the anodized alumina 202. Microscopic photograph of FIG. 4 shows the shape of the micro-pillars thus obtained, the pillars look like cilia on the surface of the metal structure.

Then, the metal structure 210 obtained in FIG. 2E was electrochemically oxidized in an aqueous alkali solution, specifically, 2 mol/dm$^3$ of an aqueous sodium hydroxide solution to form an electrode active material 220 comprising nickel hydroxide on the surface of the micro-pillars 208 and the hole bottom of the pore 209. In this case, when nickel was converted into nickel hydroxide, since the volume increased by about twice, electrochemical oxidation was conducted for about 10 nm from the surface of nickel. The converted nickel hydroxide was obtained by electrochemically oxidizing the micro-pillars 208 comprising nickel. Instead of that, the nickel hydroxide active material may also be electrodeposited in an aqueous nickel salt solution or an aqueous nickel salt solution including a cobalt salt while using the metal structure as an electrode.

As described above, according to this example, the active material can be formed directly on the surface of micro-pillars of the metal structure comprising nickel. In the electrode of the invention, since the active material is in direct contact with the conducting skeleton, a conducting aid for connecting the active materials to each other may not be added at all. The electrode of this example is suitable as a cathode for use in alkali storage battery at high utilization ratio and high capacity density, or as an electrode for use in capacitor.

EXAMPLE 2

In this example, a metal structure comprising nickel was produced by the same method as in Example 1, and ruthenium and platinum were formed as an active material onto the surface of micro-pillars comprising nickel. Specifically, by electrodepositing a metal structure in an aqueous alkali solution containing 0.05 mol/dm$^3$ of ruthenium chloride, a ruthenium metal film was formed on the surface of the micro-pillar. Ruthenium was electrodeposited potentiostatically while measuring a current such that the surface thickness of nickel was about 5 nm.

Successively, platinum was deposited on the surface of the ruthenium metal film by electrodeposition using a pulse current in an aqueous solution containing 0.03 mol/dm$^3$ of chloroplatinate. Granular platinum could be formed on the surface of the ruthenium metal film.

Figure 5:
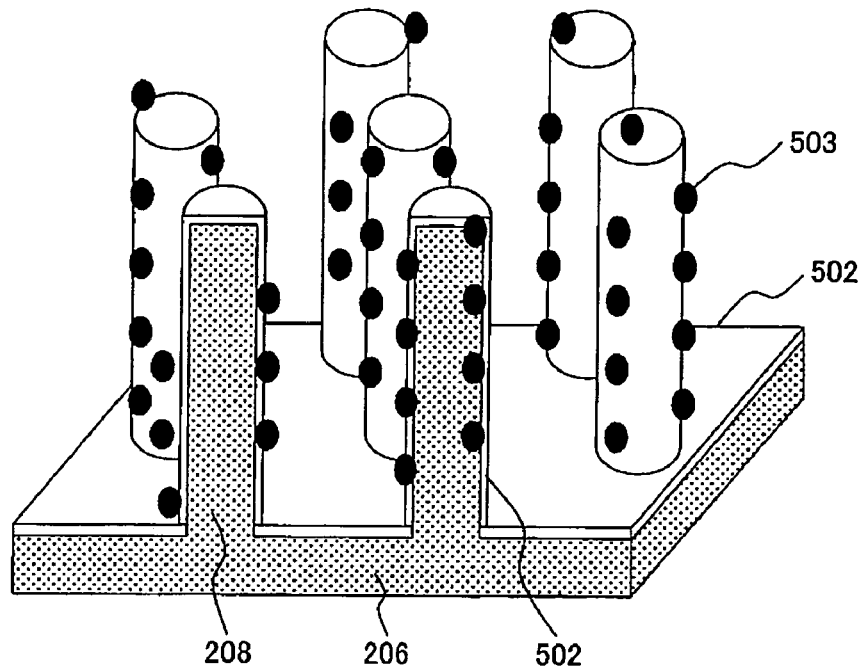
FIG. 5 is a perspective view showing another example of the electrode according to the invention.

FIG. 5 shows a perspective view of an obtained electrode. A ruthenium metal film 502 was formed directly on the surface of each micro-pillar 208 of the metal structure 210, on which granular platinum 503 was formed.

According to this example, a composite layer of platinum and ruthenium of high activity as an electrode catalyst can be formed directly on the surface of the metal structure having micro-pillars. In the electrode of the invention, since the active material is in direct contact with the conducting skeleton, the conducting aid for connecting the active materials to each other is not necessary. The electrode of this example is suitable to the use of the highly expensive noble metal at a high utilization ratio and can be provided as an electrode for a fuel cell.

EXAMPLE 3

In this example, a metal structure having micro-pillars was produced by the same method as in Example 1, and a multilayered layer comprising a ruthenium metal film and a ruthenium oxide film was formed on the surface of micro-pillars comprising nickel.

Specifically, by electrodepositing the metal structure in an aqueous alkali solution containing 0.05 mol/dm$^3$ of ruthenium chloride, a ruthenium metal film was formed on the surface. Successively, by electrochemical oxidation in a solution of sodium hydroxide, the surface portion of the ruthenium metal film was oxidized to form a ruthenium oxide film. The solution is not restricted to that of sodium hydroxide so long as it is an aqueous alkali solution.

Also in this example, since the active material can be formed directly to the conductive skeleton, a conducting aid for connecting the active materials to each other may not be added at all. The electrode of this example can be provided as a high performance capacitor electrode.

EXAMPLE 4

In this example, a metal structure having micro-pillars of nickel was produced by the same method as in Example 1, and an alloy film of nickel and tin was formed on the portion of the micro-pillars.

Specifically, an alloy of nickel and tin was formed on the surface of micro-pillars by electrodepositing the metal structure in an aqueous solution containing 0.1 mol/dm$^3$ of nickel sulfide and 0.5 mol/dm$^3$ of tin chloride. It was electrodeposited potentiostatically while measuring the current such that the thickness was about 15 nm from the surface of the micro-pillars. Successively, the metal structure was lithium-doped by supplying a cathodic current to the metal structure coated on the surface with the nickel-tin alloy, and by using an electrolyte of ethylene carbonate and diethylene carbonate mixed at ethylene carbonate : diethylene carbonate=3:7 with addition of LiClO$_4$ as a supporting salt.

According to this example, an alloy layer of nickel and tin as the elect-rode active material can be disposed directly on the surface of the metal structure comprising nickel. In this example, since the active material was in direct contact with the conducting skeleton, the conducting aid for connecting the active materials to each other may not be added at all. The electrode of this example can be provided as a negative electrode of the lithium ion secondary battery.

EXAMPLE 5

A fine porous mold was produced by the same method as in Example 1. Electroless nickel-boron alloy plating was applied on the surface of anodized alumina of the fine porous mold into a state shown in FIG. 2C. Then, the aluminum plate was removed by dissolution by the same method as in Example 1 into a state shown in FIG. 2D, nickel was filled by electroplating to a pore portion surrounded with anodized alumina, and then alumina was removed by dissolution into a state shown in FIG. 2E. Then, ruthenium and platinum were formed successively on the surface of the portion where nickel was filled in the same manner as in Example 2. Thus, an electrode having the same shape as in FIG. 5 having the active material comprising platinum and ruthenium on the surface was prepared.

Figure 8:
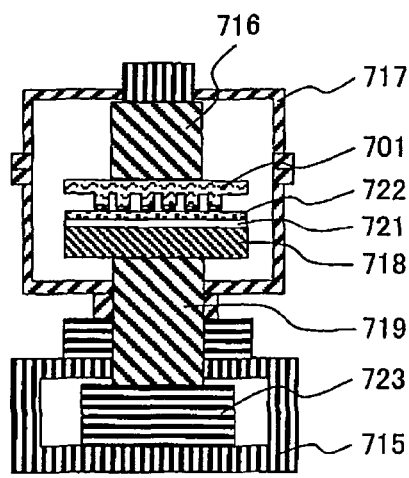
FIG. 8 is a schematic view of a device for joining a solid electrolyte and an electrode.
Figure 9:
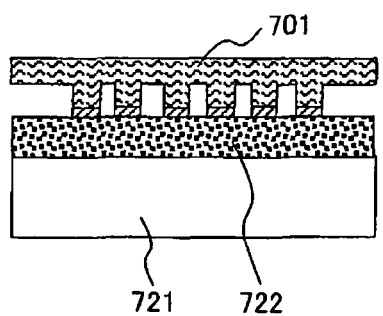
FIG. 9 is an enlarged view showing a portion of the device shown in FIG. 8 in an enlarged scale.

Then, the electrode was joined and integrated with a solid polymeric membrane. For integration, a transfer device of a structure shown in FIG. 8 and FIG. 9 was used. FIG. 8 shows the entire constitution of the transfer device which is shown in a state where an electrode 701 and a solid polymeric membrane 722 were set. FIG. 9 shows the vicinity of the electrode 701 and the solid polymeric membrane 722 in FIG. 8 in an enlarged scale.

The procedures of a process for joining the electrode and the solid polymeric membrane are to be described. At first, a process of laminating the electrode 701 and the solid polymeric membrane 722 together will be described. After positioning and combining the electrode 701, a substrate 721 and a solid polymeric membrane 722 were set on a stage 718 shown in FIG. 8. The transfer device in FIG. 8 includes a vacuum chamber 717, a frame 715, a head 716, a support 719, and a pressing mechanism 723 in which a heating mechanism is provided to the state 728. After depressurizing the vacuum chamber to 0.1 Torr and heating to 125° C., it was kept at 12 MPa and for 10 min. Then, it was allowed to cool to 100° C. or lower and then opened to atmospheric air. When the electrode was taken out of the transfer device at a room temperature, a composite body of a solid polymeric membrane and an electrode was obtained.

As the solid polymeric film, for example, a most typical polyperfluoro sulfonic acid as an ion exchange membrane for use in a fuel cell is formed into a membrane and can be used as a membrane. Examples of the polyperfluoro sulfonic acid include, for example, Nafion (trade name of products manufactured by US DuPont Co.), Flemion (trade name of products manufactured by Asahi Glass Co., Ltd.), and Aciplex (trade name of products manufactured by Asahi Kasei Corporation). In this example, a Nafion sheet was used.

Figure 6:
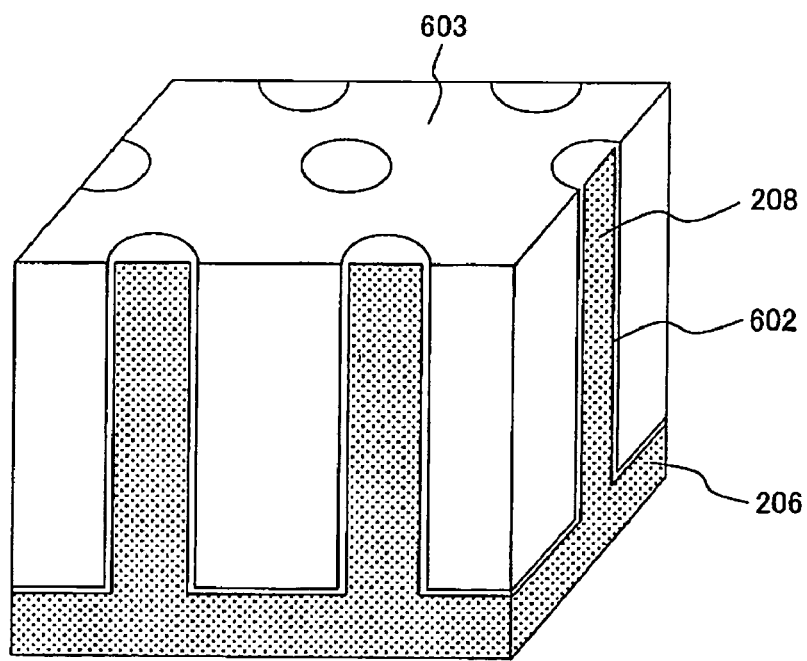
FIG. 6 is a perspective view of a solid electrolyte/electrode assembly formed by integrating a solid electrolyte and an electrode.

In accordance with the procedures described above, when the electrode was pressed to the polymeric electrolyte membrane of the Nafion sheet and press molded, a composite film in which micro-pillars of the electrode were buried in the polymeric electrolyte film could be formed. Since the metal structure having the electrode active material was formed directly to the solid polymeric membrane, there were many contacts between the electrode active material and the solid polymeric membrane, and the electrode active material could be utilized at a high utilization ratio. FIG. 6 shows a perspective view of the thus obtained solid electrolyte/electrode assembly. Micro-pillars 208 of the electrode and an electrode active material 602 are buried in a solid electrolyte 603.

Figure 7:
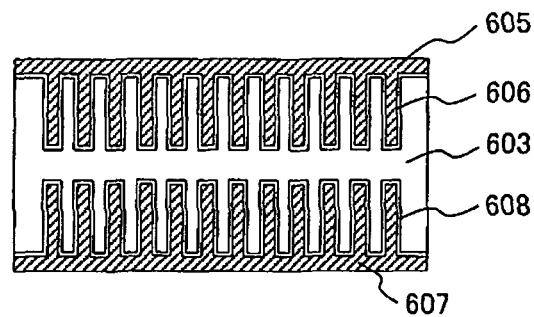
FIG. 7 is a cross sectional view showing another example of a solid electrolyte/electrode assembly.

In this example, an anode electrode and a cathode electrode of a fuel cell joined respectively to polymeric electrolyte membrane were produced and they were joined to produce a solid electrolyte/electrode assembly. This is not restrictive but an assembly of an electrolyte membrane and an electrode may also be produced by arranging electrodes on both sides of the electrolyte membrane and pressing them at the same time on both surfaces of the electrolyte membrane. FIG. 7 shows an assembly of the polymeric electrolyte membrane and the electrode obtained in this way. The assembly in FIG. 7 includes an anode electrode comprising an anode side metal film 605 and an anode side electrode active material 606, and a cathode electrode comprising a cathode side metal film 607 and a cathode side electrode active material 608. The anode and the cathode are joined to each other on both sides of the solid electrolyte 603.

According to this example, an electrode of high utilization efficiency for the expensive noble metal catalyst can be provided and the efficiency of the fuel cell can be improved. Further, the electrolyte and the electrode can be joined by a simple manufacturing technique of press molding.

EXAMPLE 6

The lithium ion secondary battery-negative electrode obtained by the production method described in Example 4 and a solid polymeric membrane were joined by a method described in Example 5 to obtain an assembly of the electrode and the solid polymeric membrane.

Typical solid polymeric membrane for use in lithium ion secondary battery includes polyethylene oxide type polymer or carbonate type polymers. In this example, polyethylene oxide was used.

According to this example, there are many contacts between the electrode active material and the solid polymeric membrane, and the electrode active substance can be utilized at a high utilization ratio. Further, an electrode with low electrode resistance and high utilization efficiency for the active material can be provided. Further, the electrolyte-electrode assembly can be obtained by a simple production technique of press molding.

EXAMPLE 7

In this example, a copper structure with micro-pillars was produced by the same method as in Example 1. Specifically, a substrate having pores was produced by applying an anodic treatment to an aluminum plate. By using the substrate as a fine porous mold, a copper layer was formed to a thickness of about 50 nm by an electroless plating method on the surface of the anodized alumina. A CAST-2000 solution produced by Hitachi Chemical Co., Ltd. was used for the electroless plating solution. Then, a copper film was formed to a thickness of 15 μm by an electroplating method using the copper layer as a seed layer. Electroplating was conducted by using a copper sulfate plating solution containing 200 g/dm$^3$ of copper sulfate and 100 g/dm$^3$ of sulfuric acid at a current density of 5 mA/cm$^2$. This is, however, not restrictive but commercial additives, etc. may also be added. Then, a pore bottom was dissolved by dissolving aluminum and applying a phosphoric acid treatment. Subsequently, copper was filled inside the pores by the same method as in the electrolytic copper plating as described above at a current density of 0.5 mA/cm$^2$. Then, remaining aluminum was dissolved in a sodium hydroxide solution to obtain a metal structure made of cupper having a group of micro-pillars.

The obtained metal structure was electrodeposited in an aqueous solution containing 0.1 mol/dm$^3$ of tin chloride to form a copper-tin alloy to the surface of copper. It was electrodeposited potentiostatically while measuring the current such that the thickness was about 15 nm from the surface of copper. Successively, it was lithium-doped by supplying a cathodic current to the metal structure coated on the surface with the copper-tin alloy by using, as an electrolyte, ethylene carbonate and diethylene carbonate mixed at ethylene carbonate : diethylene carbonate=3:7 with addition of LiClO$_4$ as a support salt.

As described above, according to this example, a copper-tin alloy layer as the electrode active material can be formed directly on the surface of the metal structure made of copper having a group of micro-pillars. In this example, since the active material is in direct contact with the conducting skeleton, the conducting aid for connecting the active materials to each other may not be added at all. The resistance value of the electrode can be lowered by using copper of low electric resistance value for the pillar structure. Such an electrode is suitable as a negative electrode for a lithium ion secondary battery.

EXAMPLE 8

In this example, a metal structure made of copper having a group of micro-pillars was produced by the same method as in Example 7. Then, the metal structure was electrodeposited in an aqueous solution containing 0.1 mol/dm$^3$ of silver cyanate to form silver on the surface of the copper. It was electrodeposited potentiostatically while measuring a current such that the thickness was about 20 nm from the surface of copper.

As described above, according to this example, a silver layer as an electrode active material can be formed directly on the surface of the metal structure made of copper. Since the active material is in direct contact with the conducting skeleton, the conducting agent for connecting the active materials each other may not be added at all. Further, expensive silver can be utilized effectively. The electrode of the example is suitable as an electrode for use in an oxygen concentration sensor.

EXAMPLE 9

In this example, a metal structure having micro-pillars made of nickel was produced in the same manner as in Example 1 and a cobalt-tin alloy film was formed on the micro-pillars.

Specifically, a cobalt-tin alloy was formed to the surface of micro-pillars by electrodepositing the metal structure in an aqueous solution containing 0.1 mol/dm$^3$ of cobalt nitrate and 0.1 mol/dm$^3$ of tin chloride. It was electrodeposited potentiostatically while measuring the current such that the thickness was about 15 nm from the surface of the micro-pillars. Successively, it was doped with lithium by supplying a cathodic current to the metal structure coated at the surface with the cobalt-tin alloy by using, as an electrolyte, ethylene carbonate and diethylene carbonate mixed at ethylene carbonate diethylene carbonate=3:7 with addition of LiClO$_4$ as a support salt.

According to this example, the cobalt-tin alloy layer as the electrode active material can be provided directly to the surface of the metal structure comprising nickel. In this example, since the active material is in direct contact with the conductive skeleton, the conducting agent for connecting the active materials to each other may not be added at all. The electrode of this example can be provided as a negative electrode for use in lithium ion secondary battery.

What is claimed is:

1. An electrode for use in an electrochemical device of converting, producing, or depositing a substance by electrochemical reaction, the electrode comprising:
   a metal structure having a major surface and a group of pillars extending from the major surface, each of the pillars having a diameter from 10 nm to 1 μm and a height of 100 nm to 50 μm, and
   an active material formed directly on the surface of the pillars and the major surface of the metal structure between the pillars such that an outer surface of the active material formed on the surface of the pillars has a shape corresponding to a shape of the pillars.

2. The electrode for use in an electrochemical device according to claim 1, wherein the pillars group like cilia on the surface of the metal structure.

3. The electrode for use in an electrochemical device according to claim 1, wherein the metal structure is formed of nickel or copper.

4. The electrode for use in an electrochemical device according to claim 1, wherein the active material is formed by depositing a metal to be the active material by plating.

5. A cathode for use in an alkaline storage battery, the cathode being constituted by the electrode according to claim 1,
   wherein the metal structure comprises nickel, and
   wherein the active material comprises nickel hydroxide formed by electrochemical oxidation.

6. An electrode for use in a capacitor, the electrode being constituted by the electrode according to claim 1, wherein the metal structure comprises nickel, and
wherein the active material comprises nickel hydroxide formed by electrochemical oxidation.

7. An electrode for use in a fuel cell, the electrode being constituted by the electrode according to claim 1,
wherein the metal structure comprises nickel, and
wherein the active material comprises ruthenium and platinum formed by electrodeposition, and the platinum Is formed on the ruthenium.

8. An electrode for use in a capacitor, the electrode being constituted by the electrode according to claim 1,
wherein the metal structure comprises nickel, and
wherein the active material comprises ruthenium formed by electrodeposition and ruthenium oxide formed by electrochemical oxidation.

9. An anode for use in a lithium ion battery, the anode being constituted by the electrode according to claim 1,
wherein the metal structure comprises nickel, and
wherein the active material comprises nickel-tin alloy or tin-cobalt alloy formed by electrodeposition, and is lithium-doped.

10. An anode for use in a lithium ion battery, the anode being constituted by the electrode according to claim 1,
wherein the metal structure comprises copper, and
wherein the active material comprises a copper-tin alloy or tin-cobalt alloy formed by electrodeposition, and is lithium-doped.

11. An electrode for use in an oxygen concentration sensor, the electrode being constituted by the electrode according to claim 1,
wherein the metal structure comprises copper, and
wherein the active material comprises silver formed by electrodeposition.

12. The electrode for use in an electrochemical device according to claim 1, wherein the pillars have a cylindrical columnar shape.

13. The electrode for use in an electrochemical device according to claim 12, wherein the pillars have a circular cylindrical shape.

14. The electrode for use in an electrochemical device according to claim 12, wherein the pillars have a square cylindrical columnar shape.

15. The electrode for use in an electrochemical device according to claim 12, wherein some of the pillars have a circular columnar shape and others of the pillars have a square cylindrical columnar shape.

* * * * *